United States Patent [19]

James et al.

[11] Patent Number: 5,210,261
[45] Date of Patent: May 11, 1993

[54] PRODUCTION OF PHOSPHOROTHIOATE SALTS

[75] Inventors: Barrie D. James, Yarm; Roger Scattergood, Reading, both of United Kingdom

[73] Assignee: Ethyl Petroleum Additives, Ltd., Bracknell, England

[21] Appl. No.: 865,679

[22] Filed: Apr. 8, 1992

Related U.S. Application Data

[63] Continuation of Ser. No. 451,455, Dec. 15, 1989, abandoned.

[30] Foreign Application Priority Data

Dec. 19, 1988 [GB] United Kingdom ............... 8829597

[51] Int. Cl.$^5$ .............................................. C07F 9/165
[52] U.S. Cl. .................................. 558/123; 558/208; 558/209; 558/210; 558/211; 558/212; 558/213
[58] Field of Search ............... 558/122, 123, 208, 209, 558/210, 211, 212, 213

[56] References Cited

U.S. PATENT DOCUMENTS

| | | | |
|---|---|---|---|
| 2,647,140 | 7/1953 | Jonas | 260/461 |
| 2,954,394 | 9/1960 | Blair et al. | 260/461 |
| 3,896,219 | 7/1975 | Pianka | 424/225 |
| 4,600,543 | 7/1986 | Bridger | 558/133 |
| 4,717,491 | 1/1988 | Cardis | 252/46.7 |
| 4,755,311 | 7/1988 | Burjes et al. | 252/49.9 |

FOREIGN PATENT DOCUMENTS 7638 12/1987 World Int. Prop. O. .

OTHER PUBLICATIONS

Chemical Abstracts Index Guide 1982–1986 N–Z p. 1393 G (1987).

*Primary Examiner*—Mukund J. Shah
*Assistant Examiner*—E. Bernhardt
*Attorney, Agent, or Firm*—David M. Bunnell

[57] ABSTRACT

Amine salts of phosphorothioic acids, useful for example in lubricant compositions, are made by forming a mixture of sulphur and an amine, and then adding a phosphite ester. The reaction is controlled by the rate of addition of the ester.

19 Claims, No Drawings

PRODUCTION OF PHOSPHOROTHIOATE SALTS

This is a continuation of copending application Ser. No. 07/451,455 filed on Dec. 15, 1989, now abandoned.

This invention relates to the production of amine salts of phosphorothioic acids, and to the salts so produced.

Amine salts of phosphorothioic acids are useful inter alia as additives for lubricants, for example as antiwear additives. They may also be used in fuels. They have previously been made by reaction of a phosphite ester first with sulphur and then with the desired amine or amines. Reference may be made for example to the processes described in U.S. Pat. Nos. 2,647,140; 4,600,543; 4,717,491; and 4,755,311. It is desirable to operate the reaction without the use of a solvent in order to avoid the expense of providing and then removing the latter.

The reaction between the phosphite ester and the sulphur is very exothermic, and it has been found that the reaction sometimes proceeds in an uncontrollably exothermic manner which can lead to breakage of equipment, loss of product, and danger to personnel. There is therefore a need to be able to produce amine salts of phosphorothioic acid in a way which is easily controlled and gives a high yield of the desired product generally suitable for use, e.g. in lubricant compositions, without further processing.

In addition, products produced in accordance with the prior processes are impure and do not in practice contain more than about 90% of the stoichiometric product. Moreover, they contain undesirable impurities such as reactive sulphur, which causes undesirable haze and corrosion of copper surfaces with which it comes in contact, and appreciable amounts of unreacted phosphite starting material (or amine salt thereof) which is liable to hydrolyse and lead to corrosion-producing products.

The present invention provides a new process which is easier to control than the previously used process and gives a higher yield of the desired product. The process is capable of giving a product which is at least 95% pure, does not contain any corrosion-causing, reactive sulphur, and has a substantially reduced content of unreacted phosphite starting material (or amine salt thereof).

The present invention provides a process for the production of an amine salt of a phosphorothioic acid, more particularly of formula:

$$(RO)_2PSO^-.HN^+R_1R_2R_3$$

in which the radicals R are the same or different and each is a substituted or unsubstituted hydrocarbyl radical of up to 20 carbon atoms each, e.g. alkyl, cycloalkyl, alkenyl, aryl or alkylaryl preferably of up to 18 carbon atoms, and especially straight or branched alkyl or alkenyl of up to 12, preferably 3 to 8, carbon atoms, or phenyl, and $R_1$, $R_2$ and $R_3$ are each hydrogen or substituted or unsubstituted hydrocarbyl radicals of up to 22 carbon atoms each, e.g. saturated or unsaturated aliphatic or cycloaliphatic radicals of up to 22 carbon atoms each, not more than two of $R_1$, $R_2$ and $R_3$ being hydrogen, which comprises:

(1) forming a mixture of sulphur, preferably in finely divided state, and the required amine or amines of formula $NR_1R_2R_3$ in the liquid state, (2) adding to the said mixture a phosphite ester of formula $(RO)_2POH$ (or a mixture of such esters) in an amount at least equivalent on a molar basis to the amount of sulphur in said mixture under conditions such that the sulphur reacts with the said ester and the reaction temperature does not rise above 130° C.

(3) continuing said reaction until solid sulphur has substantially disappeared from the reaction mixture, and, if necessary, (4) adding additional amine so that the total molar quantity of amine present is at least equivalent to the molar quantity of the phosphite ester used.

The invention also provides, as novel products, amine salts of phosphorothioic acids of formula:

$$(RO)_2PSO^-.HN^+R_1R_2R_3$$

in which R, $R_1$, $R_2$ and $R_3$ are as hereinbefore defined, the said salt having a purity of at least 95% (as measured by $^{31}P$ NMR) and containing no reactive sulphur and less than 3% unreacted phosphite of formula:

$$(RO)_2POH \text{ (also written } (RO)_2P(O)H)$$

or amine salt thereof. The substantial absence of reactive sulphur (i.e. sulphur, whether free or bound, capable of causing corrosion of copper surfaces with which the product comes in contact) may be demonstrated for example by the ASTM D-130 copper corrosion test.

In the operation of the new process, it is not necessary that all the amine required for formation of the desired salt should be initially present, but the amount initially mixed with the sulphur must be sufficient to provide a liquid reaction medium in which the sulphur can be well dispersed. More particularly, if it is desired to produce a mixed amine salt, then the less volatile amine may be used to form the initial reaction mixture and the more volatile amine added after the reaction of the sulphur with the phosphite has taken place.

The amine, sulphur and phosphite are preferably used in substantially stoichiometric quantities, but in order to avoid the presence of free sulphur in the reaction product it may be desirable to use a small excess of the phosphite ester, e.g. up to 1.1 molar equivalent of ester per molar equivalent of sulphur, and also a slight excess of amine, e.g. up to 1.2 molar equivalent of amine per molar equivalent of phosphite.

Where the amine starting material is solid at ambient temperature it may be desirable to melt it before the sulphur is added. Since amines react with sulphur and may form dark coloured products with an obnoxious odour, it is desirable to form the mixture of amine and sulphur at a temperature which is as low as possible consistent with maintaining the amine in the liquid state. The addition of a phosphite ester should begin as soon as possible after the amine and sulphur have been mixed, since once the phosphite is present in the reaction mixture, undesired reaction between the amine and the sulphur is apparently suppressed. However, it has been found that at temperatures below about 30° C., undesirable reactions between the amine and the sulphur proceed only very slowly. At temperatures above about 80° C., on the other hand, the amine and the sulphur react sufficiently rapidly to result in an undesirably dark end product with an objectionable odour.

The phosphite ester may be added to the mixture of amine (or amines) and sulphur in portions or continuously. Since the reaction is exothermic, the rate of addition of the phosphite is controlled so as to maintain the temperature of the reaction mixture at not more than 130° C., preferably below 90° C., and more preferably in the range of about 50° to 80° C.

At the end of the addition of the phosphite the reaction mixture is preferably maintained at the reaction temperature for a short period, e.g. up to 30 minutes, in order to ensure that all the sulphur present in the reaction mixture has reacted. The presence of unreacted sulphur may be detected by visual inspection since it is normally the only solid ingredient in the reaction medium. The product can generally be used without further processing.

The preferred amines for use in the present invention are saturated or unsaturated aliphatic or cycloaliphatic amines in which each of $R_1$, $R_2$ and $R_3$, which may be the same or different, is hydrogen or is an alkyl, cycloalkyl or alkenyl radical of 4 to 22 carbon atoms, not more than two of $R_1$, $R_2$ and $R_3$ being hydrogen. Primary amines are generally preferred. Mixtures of amines can be used and this can confer additional desirable properties in the product. Examples of suitable amines are primary amines such as n-butylamine, n-hexylamine, n-octylamine, n-dodecylamine, n-octadecylamine, oleylamine, 2-ethyl-n-hexylamine, t-butyl primary amine, and t-octyl primary amine, secondary amines such as di-n-octylamine and dicyclohexylamine, and tertiary amines such as N,N-di-methyl-n-octylamine. Amines derived from natural products and which therefore contain mixtures of hydrocarbyl radicals can also be used, e.g. the primary aliphatic amines usually called cocoamine and tallow amine. Commercially available mixed amines are also suitable, e.g. the products sold under the trade names PRIMENE 81-R and PRIMENE JM-T (stated by the manufacturers Rohm and Haas to be respectively mixed tertiary $C_{12}$–$C_{14}$ alkyl primary amines and mixed tertiary $C_{16}$–$C_{22}$ alkyl primary amines and referred to in Chemical Abstracts Index Guide (1982–1986) as, respectively $C_{11-14}$-tert-alkyl Amines and $C_{18-22}$-tert-alkyl Amines).

The preferred phosphite esters are dialkyl, dialkenyl, diphenyl, or di-(alkylphenyl) phosphites (in which the said alkyl and alkenyl radicals contain up to 18 carbon atoms each and the said alkylphenyl radical has up to 12 carbon atoms in the alkyl). Examples of suitable phosphites are dimethyl, di-n-butyl, di-n-octyl, di-2-ethyl-n-hexyl, dioleyl, diphenyl and di(dodecylphenyl) phosphite. Mixtures of phosphite esters can be used.

The following Examples illustrate the invention.

EXAMPLE I

PRIMENE 81-R (158 g) is placed in a 1 liter flask at room temperature (about 20° C.). Sulphur (finely powdered, 22.8 g) is then added to the amine and thoroughly mixed in. The addition of di-phenyl phosphite (175.5 g) is begun immediately. The phosphite is added at a rate such that the temperature of the reaction mixture rises to about 65° C. over 15 minutes. The rate of addition of the phosphite is then adjusted so as to maintain a temperature of 60°–70° C. during the remainder of the addition.

The reaction mixture is maintained at 60° to 70° C. for a further thirty minutes. The product is then cooled and is ready for use.

EXAMPLE II

PRIMENE 81-R (59.1 g) and oleylamine (144.5 g) are placed in a 1 liter flask and the temperature of the mixture is adjusted to 30° C. Sulphur (finely powdered, 23.9 g) is added and thoroughly mixed in. Di-n-butyl phosphite (149.4 g) is added slowly. When the temperature of the mixture has increased to about 65° C. the rate of addition of the phosphite is reduced to maintain the temperature in the range 60°–70° C. At the end of the addition, stirring is continued for 30 minutes and the mixture allowed to cool. It can be used without further processing.

EXAMPLE III

The procedure of Example II is repeated using oleylamine (227 g) in place of the mixture of PRIMENE 81-R and oleylamine. A similar product is obtained.

EXAMPLE IV

The procedure of Example II is repeated using cocoamine (180 g), sulphur (30 g) and dioleyl phosphite (582 g). After the addition of the phosphite is complete and while the mixture is at 60°–70° C., n-octylamine (32 g) is added. At the end of the addition, the temperature is maintained at 60°–70° C. for a further 30 minutes and the mixture is then allowed to cool. The product can be used without further processing.

EXAMPLE V

The procedure of Example II is repeated using N,N-dimethyldodecylamine (200 g), sulphur (23.2 g) and di-n-butyl phosphite (151 g). A similar product is obtained.

EXAMPLE VI

The procedure of Example II is repeated using oleylamine (294.8 g), sulphur (30.4 g) and dimethylphosphite (110 g). The product can be used without further processing.

EXAMPLE VII

Example I was repeated using 414.5 g of PRIMENE 81-R, 55.1 g of sulphur, and 480.4 g of technical grade di-phenyl phosphite (Aldrich Chemical Company). The reaction temperature was maintained at 80° C.

For comparison, the same starting materials in the same quantities were reacted together using the procedure described in Example 1 of U.S. Pat. No. 4,600,543 (i.e. by adding the amine to a stirred mixture of the phosphite and the sulphur), the reaction temperature being again maintained at 80° C. throughout.

The two products were examined by $^{31}P$ NMR to measure in each the relative proportions, as percentages based on the total phosphorus content, of the phosphorus present as the desired salt, the phosphorus present as diphenyl phosphite, and the phosphorus present in other phosphorus compounds. The following results were obtained:

| Phosphorus Compound | Percentage of Total Phosphorus Compounds | |
|---|---|---|
| | Process of the Invention | Process of U.S. Pat. No. 4600543 |
| PRIMENE 81-R salt of diphenyl phosphorothioate | 95 | 91 |
| Diphenyl phosphite | 2.5 | 3.8 |
| Other phosphorus-containing compounds | 2.5 | 5.2 |

The two products were also examined by the ASTM D-130 copper strip test. In this test, which provides a measure of the tendency of the tested material to corrode copper, a clean copper strip is placed in the material under test for 3 hours at 100° C. The strip is then withdrawn and compared with a standard. The following results were obtained:

| Product of the invention | 1A |
| Product of the process of U.S. Pat. No. 4600543 | 4B |

1A means that the withdrawn strip was almost clean (substantially no corrosion) while 4B means that the withdrawn strip was black (substantial corrosion).

What is claimed:

1. Process for the preparation of an amine salt of a phosphorothioic acid of formula:

$$(RO)_2PLS^-.HN^+R_1R_2R_3$$

in which the radicals R are the same or different and each is a hydrocarbyl radical of up to 20 carbon atoms and $R_1$, $R_2$ and $R_3$ are each hydrogen or hydrocarbyl radicals of up to 22 carbon atoms, not more than two of $R_1$, $R_2$ and $R_3$ being hydrogen, which comprises:
 (1) forming a mixture of sulphur and an amine or amine mixture of formula $NR_1R_2R_3$ in the liquid state,
 (2) adding to the mixture so obtained a phosphite ester of formula $(RO)_2POH$ in an amount at least equivalent on a molar basis to the amount of sulphur in said mixture under conditions such that the sulphur reacts with the said ester and the reaction temperature does not rise above 130° C., said addition being commenced sufficiently soon after the formation of said mixture of (1) whereby the formation of dark colored bodies from a reaction of said amine and said sulphur is substantially suppressed,
 (3) continuing said reaction until solid sulphur has substantially disappeared from the reaction mixture, and, if necessary,
 (4) adding additional amine so that the total molar quantity of amine present is at least equivalent to the molar quantity of the phosphite ester used.

2. Process according to claim 1 in which, in the phosphite ester, each of the R radicals is an alkyl, cycloalkyl, alkenyl, aryl or alkylaryl radical of up to 18 carbon atoms.

3. Process according to claim 1 in which R is alkyl of 3 to 8 carbon atoms or phenyl.

4. Process according to claim 1 in which R is n-butyl, n-octyl, 2-ethyl-n-hexyl, or phenyl.

5. Process according to claim 1 in which, in the amine, each of $R_1$, $R_2$ and $R_3$ is hydrogen or an alkyl, cycloalkyl or alkenyl radical of 4 to 22 carbon atoms.

6. Process according to claim 2 in which, in the amine, each of $R_1$, $R_2$ and $R_3$ is hydrogen or an alkyl, cycloalkyl or alkenyl radical of 4 to 22 carbon atoms.

7. Process according to claim 1 in which the reaction temperature is 50°-80° C.

8. Process according to claim 1 in which for each molar equivalent of sulphur the total quantity of phosphite ester used is 1 to 1.1 molar equivalent and for each molar equivalent of phosphite ester the total quantity of amine used is 1 to 1.2 molar equivalent.

9. Process according to claim 8 in which the reaction temperature is 50°-80° C.

10. Process according to claim 1 in which the reaction temperature is maintained below 90° C.

11. Process according to claim 5 in which the amine is one or a mixture of n-butylamie, n-hexylamine, n-octylamine, n-dodecylmine, n-octadecylamine, oleylamine, 2-ethyl-n-hexylamine, t-butyl primary amine, t-octyl primary amine, di-n-octylamine, dicyclohexylamine, N,N-dimethyl-n-octylamine, N,N-dimethyldodecylamine, cocoamine, tallow amine, mixed tertiary alkyl primary amine in the $C_{11}$–$C_{14}$ range, or mixed tertiary alkyl primary amine in the $C_{16}$–$C_{22}$ range.

12. Process according to claim 5 in which the amine is an alkyl primary amine or mixture thereof.

13. Process according to claim 5 in which the amine is mixed tertiary alkyl primary amine in the $C_{11}$–$C_{14}$ range or mixed tertiary alkyl primary amine in the $C_{16}$–$C_{22}$ range or mixture thereof.

14. Process according to claim 1 in which the amine of step (1) is added in less than stoichiometric quantity and the amine of step (4) is more volatile than the amine of step (1).

15. Process for the preparation of an amine salt of a phosphorothioic acid of formula:

$$(RO)_2PSO^-.HN^+H_2R_1$$

in which each of the radicals R is methyl, n-butyl, or phenyl, and in which $R_1$ is one or a mixture of n-butyl, n-hexyl, n-octyl, n-dodecyl, n-octadecyl, oleyl, 2-ethyl-n-hexyl, t-butyl, t-octyl, the hydorcarbyl radical of cocoamine, the hydrocarbyl radical of tallow amine, mixed tertiary alkyl radical in the $C_{11}$–$C_{14}$ range, or mixed tertiary alkyl radical in the $C_{16}$–$C_{22}$ range, which comprises:
 (1) forming a mixture of sulphur and an amine or amine mixture of formula $NH_2R_1$ in the liquid state,
 (2) adding to the mixture so obtained a phosphite ester of formula $(RO)_2POH$ in an amount at least equivalent on a molar basis to the amount of sulphur in said mixture under conditions such that the sulphur reacts with the said ester and the reaction temperature does not rise above 130° C., said addition being commenced sufficiently soon after the formation of said mixture of (1) whereby the formation of dark colored bodies from a reaction of said amine and said sulphur is substantially suppressed,
 (3) continuing said reaction until solid sulphur has substantially disappeared from the reaction mixture, and, if necessary,
 (4) adding additional amine so that the total molar quantity of amine present is at least equivalent to the molar quantity of the phosphite ester used.

16. Process according to claim 15 in which the reaction temperature is maintained below 90° C.

17. Process according to claim 15 in which the reaction temperature is 50°-80° C.

18. Process according to claim 15 in which for each molar equivalent of sulphur the total quantity of phosphite ester used is 1 to 1.1 molar equivalent and for each molar equivalent of phosphite ester the total quantity of amine used is 1 to 1.2 molar equivalent.

19. Process according to claim 18 in which $R_1$ is mixed tertiary alkyl radical in the $C_{11}$–$C_{14}$ range or mixed tertiary alkyl radical in the $C_{16}$–$C_{22}$ range or mixture thereof, and in which the reaction temperature is 50°-80° C.

* * * * *

UNITED STATES PATENT AND TRADEMARK OFFICE
CERTIFICATE OF CORRECTION

PATENT NO. : 5,210,261
DATED : May 11, 1993
INVENTOR(S) : Barrie D. James, et al.

It is certified that error appears in the above-identified patent and that said Letters Patent is hereby corrected as shown below:

Column 5, line 18 reads "$(RO)_2PLS^-.HN^+R_1R_2R_3$" and should read -- $(RO)_2PSO^-.HN^+R_1R_2R_3$ --

Column 6, line 4, reads "n-butylamie" and should read -- n-butylamine --

Signed and Sealed this

Third Day of May, 1994

Attest:

BRUCE LEHMAN

Attesting Officer     Commissioner of Patents and Trademarks